US00PP07831P

United States Patent [19]

Meier et al.

[11] Patent Number: Plant 7,831

[45] Date of Patent: Mar. 17, 1992

[54] BA 73-626 KENTUCKY BLUEGRASS

[75] Inventors: Virgil D. Meier; Eugene W. Mayer, both of Marysville, Ohio

[73] Assignee: The O.M. Scott & Sons Company, Inc., Marysville, Ohio

[21] Appl. No.: 542,851

[22] Filed: Jun. 22, 1990

[51] Int. Cl.[5] ..... A01H 5/00

[52] U.S. Cl. ..... Plt./88

[58] Field of Search ..... Plt./88

*Primary Examiner*—James R. Feyrer

*Attorney, Agent, or Firm*—Jones, Day, Reavis & Pogue

[57] ABSTRACT

A variety of Kentucky Bluegrass having a high level of disease resistance, good turf performance, and a very high level of seed yield potential.

1 Drawing Sheet

BACKGROUND

Kentucky Bluegrasses having been disclosed in U.S. Plant Pat. No. 3,156 which issued on May 9, 1972; U.S. Plant Pat. No. 3,186 which issued on May 23, 1972; U.S. Plant Pat. No. 4,336 which issued on Nov. 28, 1978; U.S. Plant Pat. No. 6,280 which issued on Sept. 6, 1988; U.S. Plant Pat. No. 6,537 which issued on Jan. 17, 1989; U.S. Plant Pat. No. 6,538 which issued on Jan. 17, 1989; and U.S. Plant Pat. No. 6,585 which issued Feb. 7, 1989.

SUMMARY OF THE VARIETY

The present invention relates to a new and improved variety of Kentucky Bluegrass, *Poa pratensis,* that has been designated Ba 73-626.

Ba 73-626 plant material originated by crossing a Kentucky Bluegrass plant developed and maintained in the plant nursery as the seed parent with a Kentucky Bluegrass plant selected from PI-198075, a plant introduction from Sweden available from Germplasm Services Laboratory, Beltsville, Md., as the pollen parent. As a result of this breeding, a distinct variety was produced and asexually propagated by rhizomes, tillers and disseminules. Seed of Ba 73-626 was produced first at Marysville, Ohio and later at Gervais, Oreg. This seed was used for purposes of plant turf performance evaluation trials, including those conducted under the auspices of the National Turfgrass Evaluation Program sponsored by the United States Department of Agriculture, Agricultural Research Service and the Maryland State Turfgrass Council.

Asexual reproduction of Ba 73-626 by propagules (tillers and rhizomes) and by disseminules (modified caryopses produced by apomixis) has consistently produced progeny plants indistinguishable from the mother plant. The apomixis level of Ba 73-626 ranged from 100% to 98.8% (mean of 99.4%) based upon examining seedlings from four different crop years under constant growth chamber conditions.

Ba 73-626 has a number of highly desirable characteristics including a good level of resistance to Drechslera spp. (formerly called Helminthosporium spp.) that causes leaf spot, melting out and crown rot; *Laetisaria fuciformis* that causes red thread; *Sclerotinia homoeocarpa* that causes dollar spot; Puccinia spp. that causes rust and *Phialophora gramincola* that causes summer patch (formerly called Fusairum blight). Ba 73-626 has an attractive leafy turf type growth habit; moderately wide leaf blades; attractive green color which can be maintained throughout the entire growing season; good seedling vigor and heat tolerance; good turf performance as evidenced by consistently high scores in National Turfgrass Evaluation Tests sponsored by the United States Department of Agriculture and conducted throughout the U.S.A. and Canada and a very high seed yield potential in the bluegrass seed production region of the U.S.A.

In comparison with most commercially available varieties, the new Ba 73-626 variety has a thicker peduncle, a wider and thicker flag leaf, higher seed yield, wider leaf blades and better winter color. In comparison to the pollen parent, the new variety has fewer seeds per pound, a much higher seed yield and more erect culms of mature unmowed plants.

DETAILED DESCRIPTION OF THE VARIETY

Figure 3:
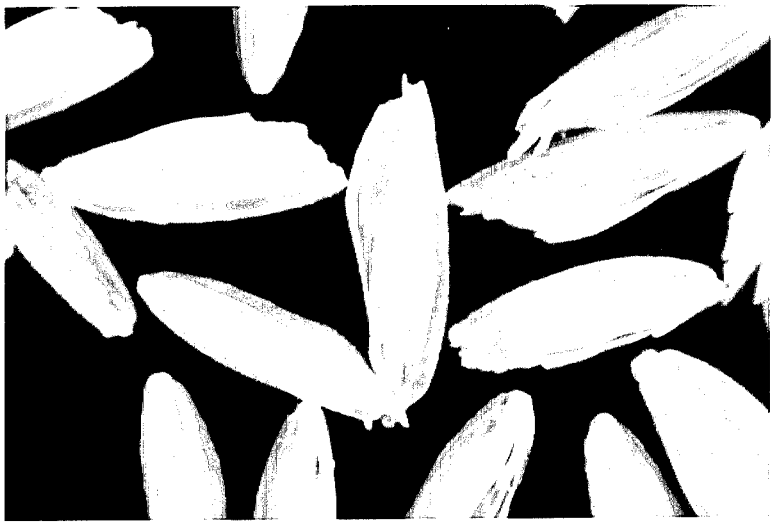
FIG. 3 shows Ba 73-626 Bluegrass seed.
Figure 2:
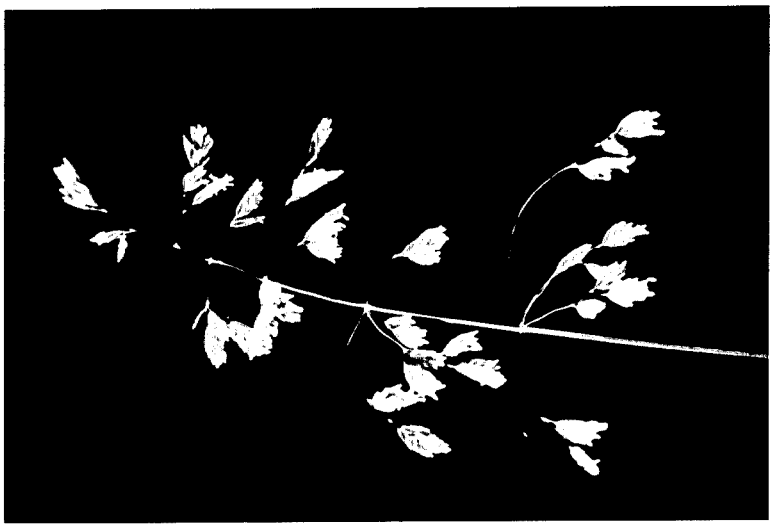
FIG. 2 shows a Ba 73-626 Kentucky Bluegrass panicle.
Figure 1:
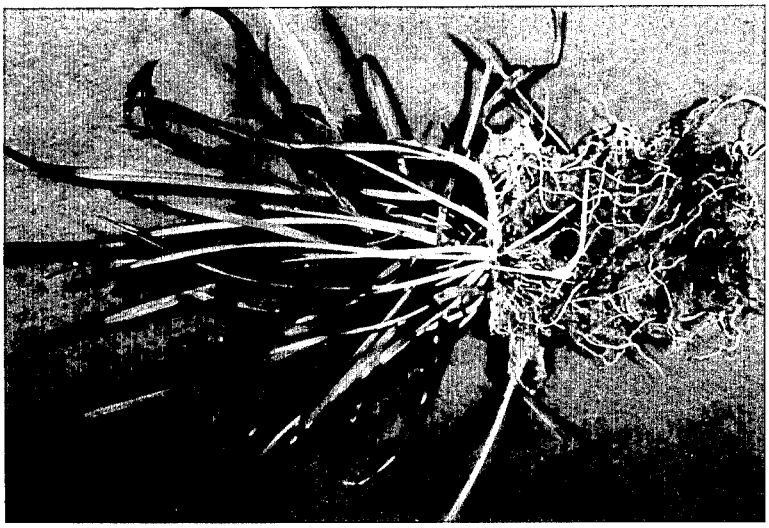
FIG. 1 shows a Ba 73-626 Kentucky Bluegrass plant in the vegetative stage including the extensive root and rhizome system.

Ba 73-626 Kentucky Bluegrass (*Poa pratensis* L.) is perennial with creeping rhizomes forming a moderately dense turf. When plants overwinter in the field with freezing temperatures and are then brought into the greenhouse during late winter to continue growth undisturbed by clipping under moderate temperatures (60°-80° F.), culms are erect averaging 514 mm in length with an average of 2.3 nodes per culm. The uppermost internode averages 12.4 cm, and the peduncle averages 12.3 cm in length, and 0.772 mm in thickness. The flag leaf averages 5.8 cm in length, 4.2 mm in width and 0.119 mm in thickness. The panicle has an average length of 9.7 cm, width of 6.0 cm, and 5.5 whorls. The lowest whorl has an average of 4.5 branches and the third whorl from the bottom of the panicle has an average of 3.4 branches. The average spikelet at the tip of a branch in the lowest whorl is 5.8 mm in length and has 4.4 florets with an outer glume of 3.2 mm and an inner glume of 3.7 mm in length. A similar spikelet from the third whorl from the bottom of the panicle is 5.6 mm in length and has 4.1 florets with an outer glume of 3.3 mm and an inner glume of 3.6 mm in length. After the seed has been conditioned, the lemma has a generally smooth keel with occasional short hairs and a few long fine hairs at the base. The seed of Ba 73-626 is 2.98 mm in length and 0.80 mm in width with approximately 921,166 seeds per pound. Comparisons of Ba 73-626 with other varieties in terms of seed dimensions and seed numbers per pound are shown in Tables 1 and 2 as follows:

TABLE 1

Seed Measurements of Ba 73-626 and Other Bluegrass Varieties After Conditioning.

| Variety | Length (mm) | Width (mm) |
|---|---|---|
| Ba 73-626 | 2.98 | 0.80 |
| Abbey | 3.18 | 0.88 |
| Coventry | 2.86 | 0.78 |
| Estate | 2.53 | 0.76 |
| Chateau | 2.77 | 0.80 |
| Baron | 3.07 | 0.86 |
| Bristol | 2.73 | 0.80 |
| Nassau | 2.96 | 0.78 |
| Newport | 2.76 | 0.71 |
| Park | 3.04 | 0.72 |
| Ram I | 3.51 | 0.84 |
| Victa | 3.20 | 0.86 |
| LSD (.05) | 0.19 | 0.06 |

TABLE 2

Comparison of Seed Numbers Per Pound of Ba 73-626 and Other Bluegrass Varieties After Conditioning.

| | Number of Seeds Per Pound |
|---|---|
| Ba 73-626 | 921,166 |
| Abbey | 1,003,037 |
| Coventry | 1,246,200 |
| Estate | 1,275,740 |
| Chateau | 1,300,105 |
| Adelphi | 1,383,976 |
| America | 1,659,824 |
| Gnome | 1,017,641 |
| Baron | 1,051,693 |
| Birka | 1,223,530 |
| Bonnieblue | 1,135,303 |
| Bristol | 1,270,821 |
| Eclipse | 1,335,668 |
| Fylking | 1,130,000 |
| Glade | 1,108,441 |
| Kenblue | 1,463,923 |
| Merit | 1,109,728 |
| Nassau | 1,127,130 |
| Newport | 1,226,481 |
| Park | 1,248,349 |
| Sydsport | 1,355,644 |
| Vantage | 1,555,303 |
| Victa | 1,038,298 |
| Windsor | 1,520,885 |

Since environmental conditions such as soil and climate may influence morphological characteristics to some extent, comparisons of morphological characteristics of Ba 73-626 are made with other Kentucky Bluegrass varieties in the following Tables 3–10:

TABLE 3

Morphological Comparison of Panicles of Ba 73-626 and Other Bluegrass Varieties in the Greenhouse at Marysville, Ohio.

| Variety | Panicle Nodding* | Panicle Length (cm) | Panicle Width (cm) | No. of Whorls Per Panicle | No. of Branches Lower Whorl | No. of Branches Third Whorl |
|---|---|---|---|---|---|---|
| Ba 73-626 | 1.3 | 9.7 | 6.0 | 5.5 | 4.5 | 3.4 |
| Abbey | 1.4 | 7.6 | 4.2 | 5.2 | 4.0 | 2.7 |
| Baron | 1.0 | 7.8 | 4.1 | 5.2 | 3.8 | 2.5 |
| Bristol | 2.0 | 9.7 | 5.0 | 5.0 | 3.3 | 2.7 |
| Chateau | 2.0 | 6.8 | 3.8 | 5.0 | 4.0 | 2.4 |
| Coventry | 2.0 | 6.7 | 3.7 | 4.8 | 3.8 | 2.7 |
| Estate | 1.2 | 7.5 | 4.2 | 5.5 | 4.0 | 3.0 |

TABLE 3-continued

Morphological Comparison of Panicles of Ba 73-626 and Other Bluegrass Varieties in the Greenhouse at Marysville, Ohio.

| Variety | Panicle Nodding* | Panicle Length (cm) | Panicle Width (cm) | No. of Whorls Per Panicle | No. of Branches Lower Whorl | No. of Branches Third Whorl |
|---|---|---|---|---|---|---|
| Nassau | 2.0 | 10.0 | 6.0 | 5.0 | 3.0 | 2.0 |
| Newport | 2.0 | 10.3 | 4.4 | 4.5 | 2.3 | 2.3 |
| Park | 1.6 | 9.0 | 3.7 | 4.0 | 4.3 | 3.7 |
| Ram I | 2.0 | 9.0 | 4.7 | 4.0 | 2.5 | 2.0 |
| Victa | 1.2 | 7.5 | 4.1 | 5.4 | 4.4 | 3.4 |
| LSD (.05) | 0.5 | 1.6 | 1.0 | 0.8 | 0.7 | 0.8 |

*Panicle nodding rated: 1 = erect, 2 = nodding

TABLE 4

Morphological Comparison of Spikelets of Ba 73-626 and Other Bluegrass Varieties in the Greenhouse at Marysville, Ohio.

| Variety | Spikelet Length (mm) Lowest Whorl | Spikelet Length (mm) Third Whorl | No. of Florets per Spikelet Lowest Whorl | No. of Florets per Spikelet Third Whorl |
|---|---|---|---|---|
| Ba 73-626 | 5.8 | 5.6 | 4.4 | 4.1 |
| Abbey | 5.1 | 5.0 | 3.9 | 3.8 |
| Baron | 5.0 | 5.0 | 3.7 | 3.8 |
| Bristol | 6.2 | 6.0 | 5.7 | 5.3 |
| Chateau | 5.1 | 5.0 | 4.2 | 3.9 |
| Coventry | 5.2 | 5.2 | 4.2 | 4.0 |
| Estate | 5.2 | 5.0 | 4.2 | 4.2 |
| Nassau | 4.6 | 4.6 | 4.5 | 4.5 |
| Newport | 5.3 | 5.2 | 5.2 | 5.2 |
| Park | 6.5 | 6.7 | 5.2 | 4.7 |
| Ram I | 4.7 | 5.2 | 5.2 | 5.5 |
| Victa | 5.2 | 5.0 | 3.8 | 3.8 |
| LSD (.05) | 0.9 | 0.8 | 1.1 | 1.0 |

TABLE 5

Morphological Comparison of Glumes of Ba 73-626 and Other Bluegrass Varieties in the Greenhouse at Marysville, Ohio.

| Variety | Glume Length (mm) Outer Lowest Whorl | Glume Length (mm) Outer Third Whorl | Glume Length (mm) Inner Lowest Whorl | Glume Length (mm) Inner Third Whorl |
|---|---|---|---|---|
| Ba 73-626 | 3.2 | 3.3 | 3.7 | 3.6 |
| Abbey | 2.9 | 2.9 | 3.3 | 3.3 |
| Baron | 2.9 | 2.8 | 3.4 | 3.3 |
| Bristol | 3.4 | 3.3 | 3.7 | 3.9 |
| Chateau | 3.1 | 3.1 | 3.4 | 3.4 |
| Coventry | 3.2 | 3.1 | 3.5 | 3.5 |
| Estate | 2.9 | 3.0 | 3.3 | 3.3 |
| Nassau | 2.3 | 2.4 | 2.7 | 2.7 |
| Newport | 2.6 | 2.5 | 2.9 | 2.9 |
| Park | 3.0 | 3.2 | 3.5 | 3.7 |
| Ram I | 2.6 | 2.4 | 2.9 | 2.7 |
| Victa | 2.8 | 3.0 | 3.3 | 3.3 |
| LSD (.05) | 0.5 | 0.4 | 0.4 | 0.4 |

TABLE 6

Morphological Comparison of Flag Leaves of Ba 73-626 and Other Bluegrass Varieties in the Greenhouse at Marysville, Ohio.

| Variety | Flag Leaf Length (cm) | Flag Leaf Width (mm) | Flag Leaf Thickness (mm) |
|---|---|---|---|
| Ba 73-626 | 5.8 | 4.2 | 0.119 |
| Abbey | 4.3 | 3.3 | 0.107 |
| Baron | 4.5 | 3.2 | 0.119 |
| Bristol | 5.5 | 3.4 | 0.127 |
| Chateau | 4.1 | 3.2 | 0.111 |
| Coventry | 4.7 | 3.2 | 0.112 |

TABLE 6-continued

Morphological Comparison of Flag Leaves of Ba 73-626 and Other Bluegrass Varieties in the Greenhouse at Marysville, Ohio.

| Variety | Flag Leaf Length (cm) | Flag Leaf Width (mm) | Flag Leaf Thickness (mm) |
|---|---|---|---|
| Estate | 5.2 | 3.6 | 0.117 |
| Nassau | 6.2 | 3.1 | 0.127 |
| Newport | 6.1 | 3.5 | 0.135 |
| Park | 4.2 | 2.6 | 0.110 |
| Ram I | 4.7 | 3.1 | 0.127 |
| Victa | 5.9 | 4.0 | 0.124 |
| LSD (.05) | 1.8 | 0.6 | 0.013 |

TABLE 7

Morphological Comparison of Peduncles, Culms, and Internodes of Ba 73-626 and Other Bluegrass Varieties in the Greenhouse at Marysville, Ohio.

| Variety | Peduncle Length (cm) | Peduncle Width (mm) | Culm Length (mm) | No. of Nodes Per Culm | Top Internode Length (cm) |
|---|---|---|---|---|---|
| Ba 73-626 | 12.3 | 0.772 | 514 | 2.3 | 12.4 |
| Abbey | 10.6 | 0.564 | 421 | 2.7 | 9.3 |
| Baron | 12.7 | 0.555 | 482 | 2.5 | 10.1 |
| Bristol | 15.0 | 0.677 | 522 | 2.7 | 11.3 |
| Chateau | 12.9 | 0.654 | 439 | 2.7 | 9.8 |
| Coventry | 13.2 | 0.607 | 435 | 2.7 | 10.2 |
| Estate | 12.6 | 0.552 | 486 | 2.2 | 10.5 |
| Nassau | 8.0 | 0.546 | 450 | 2.5 | 11.2 |
| Newport | 18.0 | 0.567 | 547 | 2.3 | 11.2 |
| Park | 14.3 | 0.779 | 578 | 3.0 | 13.0 |
| Ram I | 18.5 | 0.622 | 527 | 3.0 | 10.2 |
| Victa | 12.2 | 0.716 | 474 | 2.4 | 10.6 |
| LSD (.05) | 3.7 | 0.018 | 79 | 0.6 | 2.1 |

TABLE 8

Morphological Comparison of Leaves of Ba 73-626 and Other Bluegrass Varieties in the Greenhouse at Marysville, Ohio.

| Variety | Ligule Length (mm) | Leaf Length (mm) | Leaf Width (mm) | Leaf Angle (Degrees From Horizontal) |
|---|---|---|---|---|
| Ba 73-626 | 0.29 | 215 | 4.4 | 46 |
| Abbey | 0.23 | 218 | 3.9 | 56 |
| Baron | 0.30 | 313 | 4.4 | 63 |
| Bristol | 0.30 | 253 | 4.3 | 37 |
| Chateau | 0.25 | 204 | 4.1 | 50 |
| Coventry | 0.26 | 218 | 4.1 | 55 |
| Estate | 0.28 | 239 | 4.4 | 52 |
| Nassau | 0.22 | 226 | 3.5 | 39 |
| Newport | 0.22 | 251 | 4.1 | 50 |
| Park | 0.33 | 329 | 4.2 | 44 |
| Ram I | 0.18 | 188 | 3.7 | 40 |
| Victa | 0.28 | 235 | 4.3 | 52 |
| LSD (.05) | 0.11 | 49 | 0.6 | 10 |

TABLE 9

Morphological Comparison of Leaf Hairs of Ba 73-626 and Other Bluegrass Varieties in the Greenhouse at Marysville, Ohio.

| Variety | Hairs Around Ligule on Upper Surface of the Leaf[a] | Hairs on Collar[a] | Hairs on Ligule[b] |
|---|---|---|---|
| Ba 73-626 | 1.2 | 4.2 | 3.6 |

TABLE 9-continued

Morphological Comparison of Leaf Hairs of Ba 73-626 and Other Bluegrass Varieties in the Greenhouse at Marysville, Ohio.

| Variety | Hairs Around Ligule on Upper Surface of the Leaf[a] | Hairs on Collar[a] | Hairs on Ligule[b] |
|---|---|---|---|
| Abbey | 1.0 | 3.4 | 2.2 |
| Baron | 1.0 | 5.0 | 4.0 |
| Bristol | 1.3 | 4.7 | 4.3 |
| Chateau | 1.0 | 3.5 | 2.7 |
| Coventry | 1.0 | 3.5 | 1.5 |
| Estate | 1.0 | 3.2 | 1.3 |
| Nassau | 2.7 | 5.0 | 1.0 |
| Newport | 1.0 | 4.0 | 0.8 |
| Park | 1.0 | 1.7 | 0.0 |
| Ram I | 1.0 | 3.7 | 0.3 |
| Victa | 1.0 | 3.3 | 2.2 |
| LSD (.05) | 0.3 | 1.4 | 1.8 |

[a]Hairs around ligule and on collar rated 1–5: 1 = none, 5 = many
[b]Hairs on ligule rated 0–5: 0 = none, 5 = many

TABLE 10

Morphological Comparisons of Ba 73-626 and Other Bluegrass Varieties Grown as Unmowed Spaced Plants in the Field at Marysville, Ohio.

| | Mature Plant Height[a] | Panicle Density[b] | Maturity[c] |
|---|---|---|---|
| Ba 73-626 | 50 | 5 | 8 |
| Abbey | 49 | 5 | 7 |
| Baron | 44 | 5 | 9 |
| Coventry | 48 | 5 | 7 |
| Nassau | 46 | 6 | 9 |
| Bristol | 54 | 3 | 8 |
| Merit | 61 | 5 | 9 |
| Glade | 49 | 2 | 9 |
| Ram I | 49 | 3 | 7 |
| Victa | 54 | 6 | 8 |

Ratings:
[a]Mature Plant Height (cm) includes panicle
[b]Panicle Density - 1–10, 10 = high panicle density
[c]Maturity - 1–9, 9 = most mature No discernible differences were noted in flower parts and seed coloration other than those characteristics listed in the above tables.

Ba 73-626 has performed well in regions throughout the United States, as exhibited by high turf quality ratings in many different locations in comparison with other varieties. In addition, Ba 73-626 has a pleasant medium green color which can be maintained throughout the growing season, good winter color, and early spring greening. Comparisons of Ba 73-626 with other varieties for quality and color are set forth in Tables 11–13 hereinafter. According to comparisons with the Munsell Book for Color during mid-June, the color of Ba 73-626 leaf blades is in the range of 5 GY 4/4 to 5 GY 4/8 to 7.5 GY 4/4. During the same time period the color of similar leaf blades of several other Kentucky Bluegrass varieties—Gnome, Midnight, Bristol and Victa—fell in the same range and as a result were indistinguishable based upon use of this color dictionary. Plant age, time of year, management practices of fertilization, irrigation and mowing also influence this color range. Additional comparisons for seedling vigor, drought tolerance, leaf texture, density, seed yield and sod strength are shown in Tables 14–19.

TABLE 11

A Comparison of Turf Quality[a] of Ba 73-626 and Other Bluegrass Varieties at Various Testing Locations in the United States

| Variety | Testing Locations | | | | | | | | |
|---|---|---|---|---|---|---|---|---|---|
| | NC | KS | OH | OK | VA | IN | NE | NJ | Mean |
| Ba 73-626 | 5.0 | 7.5 | 6.7 | 5.8 | 4.9 | 6.9 | 6.1 | 5.8 | 6.1 |
| Abbey | 3.8 | 7.1 | 5.8 | 5.2 | 5.2 | 6.8 | 5.7 | 6.3 | 5.7 |
| Able I | 4.2 | 6.6 | 5.9 | 4.8 | 4.4 | 6.8 | 5.3 | 6.0 | 5.5 |
| Amazon | 3.5 | 6.9 | 6.4 | 6.2 | 4.4 | 5.0 | 4.8 | 4.9 | 5.3 |
| America | 4.3 | 7.3 | 6.8 | 4.9 | 4.8 | 6.8 | 5.0 | 5.8 | 5.7 |
| Aquila | 3.5 | 5.9 | 5.7 | 5.3 | 4.1 | 6.7 | 6.3 | 6.1 | 5.5 |
| A-34 | 3.5 | 7.4 | 6.7 | 6.3 | 4.4 | 6.8 | 5.5 | 4.3 | 5.6 |
| Baron | 5.2 | 7.5 | 6.0 | 4.8 | 4.6 | 6.8 | 5.6 | 5.3 | 5.7 |
| Barzan | 4.2 | 7.1 | 4.9 | 3.5 | 4.4 | 7.0 | 5.2 | 5.5 | 5.2 |
| Bristol | 3.7 | 7.5 | 6.7 | 5.3 | 4.4 | 6.6 | 4.7 | 6.0 | 5.6 |
| Chateau | 4.8 | 7.4 | 6.8 | 4.4 | 5.0 | 6.1 | 6.2 | 5.5 | 5.8 |
| Classic | 3.5 | 7.2 | 6.0 | 5.5 | 4.2 | 6.6 | 5.8 | 5.2 | 5.5 |
| Coventry | 3.8 | 7.2 | 6.6 | 5.1 | 5.0 | 6.5 | 5.5 | 5.2 | 5.6 |
| Estate | 4.7 | 7.0 | 6.6 | 5.3 | 4.7 | 6.5 | 5.8 | 5.8 | 5.8 |
| Georgetown | 3.8 | 7.0 | 5.9 | 4.5 | 4.5 | 6.4 | 5.4 | 4.7 | 5.3 |
| Glade | 3.8 | 7.7 | 6.6 | 3.8 | 4.8 | 7.0 | 5.7 | 5.3 | 5.6 |
| Gnome | 4.3 | 6.9 | 5.4 | 5.1 | 4.7 | 6.5 | 5.4 | 5.4 | 5.5 |
| Haga | 3.8 | 7.1 | 6.2 | 5.6 | 5.0 | 6.6 | 5.2 | 4.5 | 5.5 |
| Julia | 3.7 | 6.7 | 6.4 | 5.4 | 4.7 | 5.5 | 6.0 | 5.5 | 5.5 |
| Kenblue | 4.2 | 4.8 | 4.8 | 3.6 | 3.7 | 6.0 | 4.9 | 3.7 | 5.5 |
| Liberty | 3.8 | 7.1 | 5.9 | 4.8 | 4.5 | 6.4 | 5.2 | 5.1 | 5.4 |
| Merion | 4.0 | 7.0 | 5.9 | 3.7 | 4.3 | 6.6 | 5.9 | 4.8 | 5.3 |
| Merit | 5.2 | 7.4 | 6.2 | 4.2 | 4.6 | 7.0 | 5.6 | 5.7 | 5.7 |
| Midnight | 3.7 | 8.1 | 6.8 | 4.7 | 4.7 | 7.1 | 6.3 | 6.9 | 6.0 |
| Monopoly | 4.7 | 6.5 | 5.1 | 5.2 | 4.9 | 6.9 | 5.3 | 4.7 | 5.4 |
| Mystic | 4.2 | 6.2 | 6.4 | 3.8 | 3.4 | 7.2 | 5.7 | 5.4 | 5.3 |
| Nassau | 3.5 | 7.7 | 6.4 | 4.7 | 4.7 | 6.1 | 5.3 | 5.3 | 5.5 |
| Parade | 3.7 | 7.3 | 5.6 | 4.8 | 3.8 | 6.2 | 6.0 | 4.6 | 5.3 |
| Ram I | 4.2 | 6.5 | 6.6 | 4.9 | 4.8 | 5.8 | 5.3 | 6.0 | 5.5 |
| Rugby | 3.8 | 7.0 | 6.0 | 4.7 | 4.4 | 6.4 | 5.6 | 4.8 | 5.3 |
| Sydsport | 3.8 | 7.5 | 6.6 | 4.4 | 5.3 | 6.2 | 5.1 | 5.0 | 5.5 |
| Victa | 5.0 | 7.5 | 6.3 | 4.1 | 5.2 | 6.8 | 6.0 | 6.0 | 5.9 |
| Wabash | 4.5 | 6.7 | 5.9 | 5.1 | 4.1 | 6.8 | 6.0 | 4.0 | 5.4 |
| Welcome | 3.7 | 6.7 | 6.3 | 3.7 | 4.5 | 6.9 | 5.4 | 5.5 | 5.3 |
| LSD 0.05 | 1.1 | 0.7 | 1.0 | 1.7 | 0.8 | 0.7 | 1.0 | 1.1 | |

[a]Rating Scale 1-9: 9 = best quality

TABLE 12

A Comparison of Turf Color[a] of Ba 73-626 and Other Bluegrass Varieties at Various Testing Locations in the United States.

| Variety | Wichita Kansas | Post Falls Idaho | Silver Springs Maryland |
|---|---|---|---|
| Ba 73-626 | 7.3 | 8.0 | 8.0 |
| Abbey | 8.0 | 7.7 | 6.7 |
| Able I | 8.3 | 7.3 | 7.3 |
| Adelphi | | | 7.7 |
| Amazon | 6.0 | 7.3 | 7.7 |
| America | 8.3 | 7.7 | |
| Aquila | 8.0 | 6.0 | 6.7 |
| A-34 | 6.7 | 6.3 | 5.7 |
| Baron | 7.7 | 7.7 | 8.3 |
| Barzan | 7.0 | 6.7 | 8.0 |
| Bristol | 8.3 | 8.0 | 7.3 |
| Chateau | 7.3 | 7.0 | 7.0 |
| Classic | 6.0 | 7.0 | 6.3 |
| Coventry | 7.3 | 7.0 | 7.3 |
| Estate | 7.3 | 7.0 | 6.7 |
| Georgetown | 6.7 | 7.0 | 6.3 |
| Glade | 7.7 | 7.7 | 8.0 |
| Gnome | 7.3 | 8.0 | 7.0 |
| Haga | 6.3 | 7.0 | 5.7 |
| Julia | 7.3 | 7.7 | 7.7 |
| Kenblue | 6.0 | 6.7 | 6.0 |
| Liberty | 7.7 | 6.7 | 6.7 |
| Merion | 7.7 | 5.3 | 7.0 |
| Merit | 7.0 | 8.0 | 7.0 |
| Midnight | 8.7 | 8.0 | 8.3 |
| Monopoly | 5.3 | 6.0 | 6.0 |
| Mystic | 7.3 | 6.7 | 7.3 |
| Nassau | 7.7 | 7.3 | 7.7 |
| Parade | 7.3 | 7.3 | 6.3 |
| Ram I | 8.0 | 8.0 | 8.3 |
| Rugby | 7.0 | 6.0 | 6.0 |

TABLE 12-continued

A Comparison of Turf Color[a] of Ba 73-626 and Other Bluegrass Varieties at Various Testing Locations in the United States.

| Variety | Wichita Kansas | Post Falls Idaho | Silver Springs Maryland |
|---|---|---|---|
| Sydsport | 8.0 | 7.3 | 7.0 |
| Victa | 8.0 | 8.0 | 8.0 |
| Wabash | 6.3 | 6.0 | 6.0 |
| Welcome | 7.0 | 6.7 | 7.3 |
| LSD (.05) | 1.0 | 1.5 | 0.9 |

[a]Rating Scale 1-9: 9 = best color

TABLE 13

Winter Color[a] of Ba 73-626 and Other Bluegrass Varieties

| Variety | Testing Locations | |
|---|---|---|
| | Puyallup Washington | Agassiz British Columbia |
| Ba 73-626 | 6.0 | 4.7 |
| Abbey | 5.7 | 4.7 |
| Able I | 7.0 | 4.0 |
| Amazon | 2.7 | 4.0 |
| America | 6.3 | 4.0 |
| Aquila | 4.0 | 4.0 |
| A-34 | 6.0 | |
| Baron | 4.7 | 4.7 |
| Barzan | 2.0 | 5.0 |
| Bristol | 8.0 | 5.0 |
| Chateau | 4.3 | 5.0 |
| Classic | 6.3 | 4.0 |
| Coventry | 4.7 | 5.0 |
| Estate | 4.0 | 5.0 |
| Georgetown | 5.7 | 4.0 |

TABLE 13-continued

Winter Color[a] of Ba 73-626 and Other Bluegrass Varieties

| Variety | Testing Locations: Puyallup Washington | Agassiz British Columbia |
|---|---|---|
| Glade | 6.0 | 4.3 |
| Gnome | 5.7 | 4.3 |
| Haga | 6.0 | 4.0 |
| Julia | 6.0 | 5.0 |
| Kenblue | 1.3 | 3.0 |
| Liberty | 6.7 | |
| Merion | 6.3 | 4.0 |
| Merit | 5.7 | 5.0 |
| Midnight | 6.3 | 4.7 |
| Monopoly | 6.0 | 4.7 |
| Mystic | 1.3 | 2.7 |
| Nassau | 7.3 | 5.0 |
| Parade | 6.0 | 4.0 |
| Ram I | 3.7 | 4.7 |
| Rugby | 5.7 | 4.3 |
| Sydsport | 4.3 | 5.0 |
| Victa | 6.7 | 5.0 |
| Wabash | 3.3 | 3.3 |
| Welcome | 1.3 | 5.0 |
| LSD 0.05 | 1.6 | 0.6 |

[a]Rating Scale: 1-9 Larger number indicates greener color

TABLE 14

Comparison of Seedling Vigor[a] of Ba 73-626 and Other Bluegrasses

| Variety | Testing Location Ritzville, Washington |
|---|---|
| Ba 73-626 | 3.0 |
| Abbey | 1.3 |
| Able I | 1.7 |
| Amazon | 1.7 |
| America | 1.7 |
| Aquila | 1.3 |
| A-34 | 2.3 |
| Baron | 2.0 |
| Barzan | 2.7 |
| Bristol | 2.7 |
| Chateau | 1.7 |
| Classic | 2.3 |
| Coventry | 2.3 |
| Estate | 1.3 |
| Georgetown | 2.0 |
| Glade | 2.0 |
| Gnome | 2.3 |
| Haga | 2.3 |
| Julia | 1.7 |
| Kenblue | 1.3 |
| Liberty | 1.7 |
| Merion | 1.3 |
| Merit | 1.3 |
| Midnight | 1.0 |
| Monopoly | 2.0 |
| Mystic | 2.7 |
| Nassau | 2.0 |
| Parade | 1.0 |
| Ram I | 2.0 |
| Rugby | 1.7 |
| Sydsport | 1.7 |
| Victa | 3.0 |
| Wabash | 1.0 |
| Welcome | 1.7 |
| LSD 0.05 | 1.3 |

[a]Rating Scale: 1-9 9 = most vigor

TABLE 15

Comparison of Drought and Heat Tolerance[a] of Ba 73-626 and Other Bluegrasses

| Variety | Testing Locations: Post Falls Idaho | Marysville Ohio |
|---|---|---|
| Ba 73-626 | 7.7 | 6.3 |

TABLE 15-continued

Comparison of Drought and Heat Tolerance[a] of Ba 73-626 and Other Bluegrasses

| Variety | Testing Locations: Post Falls Idaho | Marysville Ohio |
|---|---|---|
| Abbey | 7.7 | 6.3 |
| Able I | 7.7 | |
| Adelphi | | 5.7 |
| Amazon | 7.0 | |
| America | 8.0 | |
| Aquila | 7.3 | |
| A-34 | 6.0 | |
| Baron | 7.0 | 6.0 |
| Barzan | 6.0 | |
| Bonnieblue | | 6.0 |
| Bristol | 6.7 | 6.0 |
| Chateau | 7.0 | 6.0 |
| Classic | 7.3 | 5.3 |
| Coventry | 7.3 | 6.0 |
| Estate | 7.0 | 6.0 |
| Georgetown | 6.7 | 4.7 |
| Glade | 6.7 | 6.3 |
| Gnome | 8.0 | 6.3 |
| Haga | 6.7 | |
| Julia | 7.3 | |
| Kenblue | 6.3 | |
| Liberty | 7.7 | |
| Merion | 7.3 | 5.0 |
| Merit | 8.0 | 6.0 |
| Midnight | 6.0 | |
| Monopoly | 6.7 | |
| Mystic | 7.7 | |
| Nassau | 8.0 | 6.0 |
| Newport | | 6.0 |
| Parade | 5.7 | |
| Park | | 5.0 |
| Ram I | 8.7 | 6.0 |
| Rugby | 7.0 | |
| Sydsport | 7.0 | |
| Vantage | | 6.0 |
| Victa | 7.7 | |
| Wabash | 6.7 | 4.0 |
| Welcome | 7.3 | |
| LSD 0.05 | 1.7 | 0.9 |

[a]1-9 Scale 9 = most tolerant

TABLE 16

Comparison of Leaf Texture[a] of Ba 73-626 and Other Bluegrasses Under Mowed Conditions

| Variety | Testing Locations: Puyallup Washington | Agassiz British Columbia |
|---|---|---|
| Ba 73-626 | 3.7 | 5.3 |
| Abbey | 5.3 | 5.7 |
| Able I | 7.7 | 6.0 |
| Amazon | 6.0 | 6.3 |
| America | 7.7 | 6.0 |
| Aquila | 7.0 | 6.0 |
| A-34 | 6.7 | 5.7 |
| Baron | 4.3 | 6.0 |
| Barzan | 5.7 | 6.0 |
| Bristol | 6.0 | 5.0 |
| Chateau | 4.3 | 5.7 |
| Classic | 7.3 | 6.0 |
| Coventry | 4.3 | 5.3 |
| Estate | 4.7 | 5.7 |
| Georgetown | 8.0 | 5.3 |
| Glade | 6.7 | 6.0 |
| Gnome | 5.3 | 5.3 |
| Haga | 7.7 | 6.0 |
| Julia | 6.0 | 6.0 |
| Kenblue | 5.3 | 6.7 |
| Liberty | 6.0 | |
| Merion | 8.0 | 6.0 |
| Merit | 4.0 | 6.0 |
| Midnight | 6.0 | 6.0 |
| Monopoly | 7.0 | 6.0 |
| Mystic | 6.0 | 7.3 |

TABLE 16-continued

Comparison of Leaf Texture[a] of Ba 73-626 and Other Bluegrasses Under Mowed Conditions

| Variety | Testing Locations: Puyallup Washington | Agassiz British Columbia |
|---|---|---|
| Nassau | 7.0 | 5.0 |
| Parade | 7.0 | 6.0 |
| Ram I | 6.3 | 6.3 |
| Rugby | 6.3 | 6.0 |
| Sydsport | 5.0 | 6.0 |
| Victa | 3.3 | 5.7 |
| Wabash | 7.0 | 6.3 |
| Welcome | 6.3 | 6.0 |
| LSD 0.05 | 1.4 | 0.6 |

[a]Rating Scale 1-9 9 = finest leaf

TABLE 17

A Comparison of the Average Spring and Summer Density[a] of Ba 73-626 and Other Bluegrasses at Various Locations[b]

| Variety | Spring | Summer |
|---|---|---|
| Ba 73-626 | 6.1 | 7.2 |
| Abbey | 6.3 | 7.2 |
| Baron | 6.1 | 7.2 |
| Chateau | 6.6 | 7.3 |
| Classic | 6.9 | 7.3 |
| Coventry | 6.7 | 7.3 |
| Estate | 6.1 | 7.3 |
| Glade | 5.9 | 7.3 |
| Gnone | 5.8 | 6.9 |
| Kenblue | 5.9 | 6.8 |
| Merion | 6.3 | 6.9 |
| Merit | 6.0 | 6.9 |
| Midnight | 6.1 | 7.7 |
| Nassau | 5.7 | 6.8 |
| Parade | 6.2 | 7.3 |
| Ram I | 6.6 | 7.3 |
| Victa | 5.8 | 7.1 |
| LSD 0.05 | 0.8 | 0.6 |

[a]Rating Scale 1-9: 9 = Maximum
[b]The testing locations were in Indiana, Ohio and Manitoba, Canada for both spring and summer testing.

TABLE 18

Seed Yield Comparisons[a] of Ba 73-626 and Other Bluegrass Varieties in Gervais, Oregon

| Variety | Year 1 | Year 2 | Year 3 | Year 4 |
|---|---|---|---|---|
| Ba 73-626 | 672 | 1136 | 760 | 1265 |
| Abbey | 691 | 1586 | | |
| Bristol | 347 | 808 | 627 | 684 |
| Chateau | 559 | 757 | | |
| Coventry | 643 | 930 | | |
| Estate | 585 | 864 | | |
| Julia | 296 | 1016 | | |
| Mosa | 322 | 1060 | | |
| Newport | 435 | 1256 | | |
| Victa | 780 | 1394 | 855 | 1287 |
| LSD 0.05 | 140 | 134 | 105 | 131 |

[a]Seed yields: Pounds per acre

TABLE 19

Comparison of Sod Strength[a] of Ba 73-626 and Other Bluegrasses under Mowed Conditions

| Variety | Testing Location Remington, Virginia |
|---|---|
| Ba 73-626 | 14.3 |
| A-34 | 9.7 |
| Able I | 8.7 |
| Amazon | 8.7 |
| America | 18.7 |
| Aquila | 16.3 |
| Baron | 14.7 |
| Barzan | 8.3 |
| Bristol | 8.3 |

TABLE 19-continued

Comparison of Sod Strength[a] of Ba 73-626 and Other Bluegrasses under Mowed Conditions

| Variety | Testing Location Remington, Virginia |
|---|---|
| Chateau | 15.0 |
| Classic | 15.3 |
| Coventry | 11.0 |
| Estate | 16.0 |
| Georgetown | 14.3 |
| Glade | 18.0 |
| Gnome | 14.3 |
| Haga | 13.0 |
| Julia | 11.0 |
| Kenblue | 16.3 |
| Liberty | 11.0 |
| Merion | 11.3 |
| Merit | 13.3 |
| Midnight | 14.3 |
| Monopoly | 8.3 |
| Mystic | 14.3 |
| Nassau | 8.3 |
| Parade | 12.7 |
| Ram I | 11.0 |
| Rugby | 11.7 |
| Sydsport | 20.7 |
| Victa | 16.3 |
| Wabash | 10.3 |
| Welcome | 18.0 |
| LSD (0.05) | 6.1 |

[a]Sod strength measured in kilograms of tension needed to tear sod.

Turf diseases are one of the major causes of inconsistent and poor turf performance. Ba 73-626 has been found to have a high level of resistance to leaf spot (also known as melting out and crown rot) caused by *Drechslera poae* (formerly called *Helminthosporium vagans*), a medium to high level of resistance to rust caused by Puccinia spp., to dollarspot caused by *Sclerotinia homoeocarpa,* to red thread caused by *Laetisaria fuciformis* formerly called Corticium, to summer patch caused by *Phialophora graminicola* formerly called a Fusarium spp and to necrotic ring spot caused by *Leptosphaeria korrae.*

Comparisons of Ba 73-626 with other varieties regarding resistance to leaf spot, rust, dollarspot, red thread and summer patch are presented in Tables 20–23.

TABLE 20

Comparison of Leafspot Disease Incidence on Ba 73-626 And Other Bluegrasses

| Variety | Testing Locations: Marysville Ohio[a] | Blacksburg Virginia[b] | Puyallup Washington[b] |
|---|---|---|---|
| Ba 73-626 | 8.3 | 6.0 | 8.3 |
| Abbey | | 6.0 | 8.0 |
| Able I | | 4.7 | 9.0 |
| Adelphi | 20.0 | | |
| Amazon | | 5.3 | 7.0 |
| America | | 5.3 | 8.7 |
| Aquila | | 4.3 | 7.3 |
| A-34 | | 5.3 | 8.7 |
| Baron | 10.0 | 5.7 | 8.3 |
| Barzan | | 5.3 | 3.3 |
| Bonnieblue | 13.3 | | |
| Bristol | | 5.7 | 9.0 |
| Chateau | | 5.7 | 9.0 |
| Classic | | 5.3 | 8.7 |
| Coventry | 11.7 | 5.7 | 9.0 |
| Estate | | 5.3 | 9.0 |
| Georgetown | | 5.7 | 9.0 |
| Glade | 11.7 | 5.5 | 8.0 |
| Gnome | | 5.7 | 8.7 |
| Haga | | 5.7 | 9.0 |
| Julia | | 6.0 | 9.0 |
| Kenblue | | 2.3 | 1.0 |

TABLE 20-continued

Comparison of Leafspot Disease Incidence on Ba 73-626 And Other Bluegrasses

| Variety | Testing Locations: Marysville Ohio[a] | Blacksburg Virginia[b] | Puyallup Washington[b] |
|---|---|---|---|
| Liberty | | 5.7 | 8.7 |
| Merion | 18.3 | 6.0 | 9.0 |
| Merit | 20.3 | 6.0 | 8.3 |
| Midnight | | 5.3 | 9.0 |
| Monopoly | | 4.7 | 8.0 |
| Mystic | | 4.7 | 1.0 |
| Nassau | | 6.0 | 9.0 |
| Newport | 46.7 | | |
| Parade | | 4.3 | 9.0 |
| Park | 60.0 | | |
| Ram I | 16.7 | 5.0 | 5.3 |
| Rugby | | 4.7 | 9.0 |
| Sydsport | 11.7 | 6.3 | 9.0 |
| Vantage | 45.0 | | |
| Victa | 15.0 | 6.0 | 8.0 |
| Wabash | | 2.3 | 6.3 |
| Welcome | | 4.3 | 1.3 |
| LSD 0.05 | 17.6 | 1.1 | 1.6 |

[a]Results expressed in % of turf affected by disease
[b]Results rated on scale of 1-9: 9 = least disease

TABLE 21

Comparison of Stem and Leaf Rust[a] (Puccinia spp.) Disease Incidence on Ba 73-626 and Other Bluegrasses

| Variety | Testing Locations: Adelphia New Jersey Stem Rust | Riverside California Leaf Rust | Post Falls Idaho Leaf Rust |
|---|---|---|---|
| Ba 73-626 | 7.3 | 5.7 | 8.7 |
| Abbey | 6.3 | 5.3 | 8.3 |
| Able I | 7.0 | 6.3 | 8.3 |
| Amazon | 6.0 | 5.3 | 7.7 |
| America | 8.3 | 6.0 | 8.7 |
| Aquila | 8.0 | 5.7 | 7.7 |
| A-34 | 8.0 | 6.3 | 7.7 |
| Baron | 7.3 | 5.0 | 8.0 |
| Barzan | 8.0 | 5.7 | 7.7 |
| Bristol | 8.7 | 6.0 | 8.7 |
| Chateau | 8.3 | 5.3 | 8.0 |
| Classic | 8.7 | 6.0 | 9.0 |
| Coventry | 8.3 | 5.0 | 7.3 |
| Estate | 7.3 | 5.7 | 8.0 |
| Georgetown | 9.0 | 6.0 | 8.3 |
| Glade | 7.7 | 5.0 | 8.7 |
| Gnome | 7.7 | 5.3 | 8.3 |
| Haga | 9.0 | 6.3 | 8.3 |
| Julia | 8.0 | 5.7 | 8.0 |
| Kenblue | 8.3 | 5.7 | 7.7 |
| Liberty | 8.3 | 6.7 | 8.0 |
| Merion | 2.7 | 4.0 | 6.7 |
| Merit | 8.0 | 5.7 | 9.0 |
| Midnight | 8.3 | 5.7 | 7.7 |
| Monopoly | 8.0 | 5.3 | 8.3 |
| Mystic | 5.3 | 5.7 | 7.3 |
| Nassau | 7.7 | 5.7 | 8.0 |
| Parade | 9.0 | 7.0 | 7.7 |
| Ram I | 8.7 | 6.0 | 8.7 |
| Rugby | 8.7 | 6.7 | 8.3 |

TABLE 21-continued

Comparison of Stem and Leaf Rust[a] (Puccinia spp.) Disease Incidence on Ba 73-626 and Other Bluegrasses

| Variety | Testing Locations: Adelphia New Jersey Stem Rust | Riverside California Leaf Rust | Post Falls Idaho Leaf Rust |
|---|---|---|---|
| Sydsport | 8.0 | 5.3 | 8.3 |
| Victa | 7.7 | 4.7 | 7.3 |
| Wabash | 8.0 | 5.3 | 8.0 |
| Welcome | 7.3 | 6.0 | 8.3 |
| LSD 0.05 | 1.0 | 1.5 | 1.4 |

[a]Results rated on a scale of 1-9: 9 = least disease

TABLE 22

A Comparison of Red Thread, Summer Patch, Necrotic Ring Spot and Dollar Spot[a] Incidence Level on Ba 73-626 and Other Bluegrasses at Various Locations in the United States.

| Variety | Testing Locations: Blacksburg, Virginia Red Thread | West Lafayette, Indiana Summer Patch | Hubbard, Oregon Necrotic Ring Spot | Columbia, Missouri Dollarspot |
|---|---|---|---|---|
| Ba 73-626 | 5.7 | 9.0 | 6.3 | 7.7 |
| Abbey | 6.0 | 8.0 | 6.0 | 6.7 |
| Able I | 3.7 | 8.7 | 7.3 | 6.3 |
| Amazon | 3.0 | 4.3 | 5.0 | 5.7 |
| America | 5.3 | 9.0 | 7.0 | 7.0 |
| Aquila | 3.7 | 9.0 | 6.0 | 7.7 |
| A-34 | 4.3 | 8.3 | 5.0 | 7.3 |
| Baron | 4.7 | 8.7 | 5.3 | 7.7 |
| Barzan | 4.0 | 8.0 | 6.0 | 6.0 |
| Bristol | 5.7 | 9.0 | 6.0 | 7.3 |
| Chateau | 4.7 | 6.7 | 5.0 | 6.0 |
| Classic | 5.0 | 8.7 | 4.7 | 6.7 |
| Coventry | 5.0 | 7.3 | 6.3 | 7.7 |
| Estate | 4.3 | 7.3 | 6.7 | 7.3 |
| Georgetown | 4.7 | 8.7 | 5.7 | 6.7 |
| Glade | 3.3 | 9.0 | 7.0 | 6.7 |
| Gnome | 4.0 | 7.0 | 6.7 | 7.7 |
| Haga | 4.0 | 9.0 | 5.3 | 7.7 |
| Julia | 3.0 | 5.3 | 7.3 | 6.7 |
| Kenblue | 2.7 | 8.3 | 6.7 | 7.0 |
| Liberty | 4.3 | 8.7 | 6.0 | 7.0 |
| Merion | 3.3 | 8.0 | 7.7 | 7.3 |
| Merit | 4.0 | 9.0 | 6.0 | 5.0 |
| Midnight | 5.0 | 9.0 | 7.3 | 5.7 |
| Monopoly | 5.7 | 9.0 | 5.0 | 7.0 |
| Mystic | 1.7 | 9.0 | 6.7 | 7.3 |
| Nassau | 4.3 | 7.3 | 6.0 | 6.0 |
| Parade | 5.0 | 7.3 | 5.0 | 6.3 |
| Ram I | 4.3 | 4.3 | 7.0 | 4.3 |
| Rugby | 4.7 | 8.7 | 5.3 | 7.3 |
| Sydsport | 4.3 | 7.3 | 6.7 | 6.7 |
| Victa | 5.7 | 8.0 | 6.3 | 7.0 |
| Wabash | 3.3 | 9.0 | 4.7 | 5.7 |
| Welcome | 4.0 | 8.3 | 6.0 | 8.3 |
| LSD 0.05 | 1.4 | 2.6 | 1.0 | 1.9 |

[a]Results rated on scale of 1-9: 9 = least disease

What is claimed is:

1. A variety of Kentucky Bluegrass plant, substantially as shown and described, characterized by a medium to high level of resistance to several serious diseases, including leaf spot disease, a desirable green color throughout the growing season, a strong sodformer, a high quality dense persistent turf under a wide variety of environmental conditions and a high level of seed yielding capacity.

* * * * *